(12) United States Patent  (10) Patent No.: US 8,142,353 B2
Pecherer et al.  (45) Date of Patent: Mar. 27, 2012

(54) METAL LARYNGOSCOPE BLADE WITH ILLUMINATION ASSEMBLY

(75) Inventors: Eugeny Pecherer, Netanya (IL); Igor Kobets, Pardes Hanna (IL)

(73) Assignee: Truphatek International Ltd. (IL)

( * ) Notice: Subject to any disclaimer, the term of this patent is extended or adjusted under 35 U.S.C. 154(b) by 487 days.

(21) Appl. No.: 12/458,366

(22) Filed: Jul. 9, 2009

(65) Prior Publication Data

US 2010/0041953 A1  Feb. 18, 2010

Related U.S. Application Data (63) Continuation-in-part of application No. 10/588,060, filed on Aug. 1, 2006, now Pat. No. 7,736,304.

(30) Foreign Application Priority Data

Jul. 17, 2008 (IL) .......................................... 192873

(51) Int. Cl.
*A61B 1/267* (2006.01)
(52) U.S. Cl. ......... 600/199; 600/185; 600/198; 600/197
(58) Field of Classification Search ........... 600/185–200
See application file for complete search history.

(56) References Cited

U.S. PATENT DOCUMENTS

| 2,433,705 A | 12/1947 | Palmeter |
| 3,426,749 A | 2/1969 | Jephcott |
| 3,598,113 A | 8/1971 | Moore et al. |
| 3,766,909 A | 10/1973 | Ozbey |
| 3,826,248 A | 7/1974 | Gobels |
| 3,856,001 A | 12/1974 | Phillips |
| 3,874,371 A | 4/1975 | Stader et al. |
| 4,037,588 A | 7/1977 | Heckele |
| 4,406,280 A | 9/1983 | Upsher |
| 4,437,458 A | 3/1984 | Upsher |
| 4,527,553 A | 7/1985 | Upsher |
| 4,556,052 A | 12/1985 | Muller |
| 4,557,256 A | 12/1985 | Bauman |
| 4,565,187 A | 1/1986 | Soloway |
| 4,570,614 A | 2/1986 | Bauman |
| 4,579,108 A | 4/1986 | Bauman |

(Continued)

FOREIGN PATENT DOCUMENTS

DE  26 21 232  11/1977

(Continued)

OTHER PUBLICATIONS

Hilbro brochure, Green System Fiber Optic Laryngoscope, Interchangeable Light Guide Insert, Oct. 2001.

(Continued)

*Primary Examiner* — Thomas C. Barrett
*Assistant Examiner* — Christine Nelson
(74) *Attorney, Agent, or Firm* — Abraham Hershkovitz; Harold L. Novick; Hershkovitz & Associates, LLC (57) ABSTRACT

Metal laryngoscope blade including a resiliently elastically deformable metal blade hook-on fitting for removable double snap engagement into an operative intubation position on a metal laryngoscope handle with a correspondingly sized handle hook-on fitting, a metal spatula attached to the blade hook-on fitting and including a leading tip for transversely extending from the laryngoscope handle in the operative intubation position for insertion into a subject's mouth, and an illumination assembly including an electrical light source disposed toward the leading tip for providing illumination thereat for assisting intubation.

7 Claims, 7 Drawing Sheets

U.S. PATENT DOCUMENTS

| | | | |
|---|---|---|---|
| 4,583,527 A | 4/1986 | Musicant et al. |
| 4,596,239 A | 6/1986 | Bauman |
| 4,679,547 A | 7/1987 | Bauman |
| 4,878,486 A | 11/1989 | Slater |
| 4,884,558 A | 12/1989 | Gorski et al. |
| 4,924,855 A | 5/1990 | Salerno et al. |
| 4,930,495 A | 6/1990 | Upsher |
| 4,958,624 A | 9/1990 | Stone et al. |
| 4,972,825 A | 11/1990 | Vescovo, Jr. |
| 5,060,633 A | 10/1991 | Gibson |
| 5,065,738 A | 11/1991 | Van Dam |
| 5,178,131 A | 1/1993 | Upsher |
| 5,355,870 A | 10/1994 | Lacy |
| 5,501,651 A | 3/1996 | Bauman |
| 5,529,570 A | 6/1996 | Storz |
| 5,651,760 A | 7/1997 | Upsher |
| 5,702,351 A | 12/1997 | Bar-Or et al. |
| 5,776,053 A | 7/1998 | Dragisic et al. |
| 5,873,818 A | 2/1999 | Rothfels |
| 5,879,304 A | 3/1999 | Shuchman et al. |
| 6,013,026 A | 1/2000 | Krauter et al. |
| 6,139,491 A | 10/2000 | Heine et al. |
| 6,213,937 B1 | 4/2001 | Vivenzio |
| RE37,861 E | 9/2002 | Schneider |
| 6,508,759 B1 | 1/2003 | Taylor et al. |
| 6,719,688 B2 | 4/2004 | Pecherer et al. |
| 7,128,710 B1 | 10/2006 | Cranton et al. |
| 7,214,184 B2 | 5/2007 | McMorrow |
| 2002/0082477 A1 | 6/2002 | Kim |
| 2003/0092967 A1 | 5/2003 | Fourie et al. |
| 2004/0122292 A1 | 6/2004 | Dey et al. |
| 2004/0127770 A1 | 7/2004 | McGrath, Jr. |
| 2004/0215062 A1 | 10/2004 | Dalle et al. |
| 2005/0090712 A1 | 4/2005 | Cubb |
| 2007/0093693 A1 | 4/2007 | Geist et al. |

FOREIGN PATENT DOCUMENTS

| | | |
|---|---|---|
| DE | 202 18 560 | 5/2003 |
| GB | 685741 | 1/1953 |
| GB | 806467 | 12/1958 |
| WO | WO 2006/131770 | 12/2006 |

OTHER PUBLICATIONS

Medizintechnik KaWe Germany, Laryngoskope, Megalight F.O.

International Search Report (ISR) mailed Sep. 25, 2007, in International Publication No. WO 2006/056976.

International Search Report (ISR) mailed Oct. 31, 2008, in International Publication No. WO 2008/111057.

International Search Report (ISR) mailed Nov. 13, 2008, in International Publication No. WO 2009/019703.

METAL LARYNGOSCOPE BLADE WITH ILLUMINATION ASSEMBLY

CROSS-REFERENCE TO RELATED APPLICATIONS

The present application claims priority on an Israel patent application serial number 192,873 filed on Jul. 17, 2008, incorporated herein by reference; and is a continuation in part application of U.S. patent application Ser. No. 10/588,060 filed Aug. 1, 2006 now U.S Pat. No. 7,735,304, incorporated herein by reference.

FIELD OF THE INVENTION

The present application pertains to metal laryngoscope blades with illumination assemblies including an electrical light source for providing illumination for assisting intubation.

BACKGROUND OF THE INVENTION

Commonly assigned US Patent Application Publication No. US 2007/0129606 A1 entitled Metal Laryngoscope Blade illustrates and describes metal laryngoscope blades with a resiliently elastically deformable metal blade hook-on fitting for removable double snap engagement into an operative intubation position on a metal laryngoscope handle with a correspondingly sized handle hook-on fitting.

US 2007/0129606 A1's FIGS. 1 and 2 show an ISO 7376/3 type laryngoscope (1) including an ISO 7376/3 type laryngoscope blade (2) for removable double snap fit engagement into an operative intubation position on an ISO 7376/3 type metal laryngoscope handle (4) having an electrical light source (6) in selective electrical connection with an electrical power source stored therein on depression theretoward. The ISO 7376/3 type laryngoscope blade (2) includes an L-shaped light guide mount (9) employed for transferring illumination light from the electrical light source (6) towards a subject's larynx entrance area.

US 2007/0129606 A1's FIGS. 5 and 6 show ISO 7376/1 type laryngoscopes (31) and (41) including an ISO 7376/1 type laryngoscope blade (32) for removable double snap fit engagement into an operative intubation position on an ISO 7376/1 type metal laryngoscope handle (33) having an exposed electrical contact (34). The ISO 7376/1 type laryngoscope (31) includes a light guide mount (37) for selectively contacting an electrical light source (38) disposed toward the laryngoscope blade's leading tip (39) with the electrical contact (34) in its operative intubation position for assisting intubation. The ISO 7376/1 type laryngoscope (41) includes a light guide mount (43) with an electrical light source (44) disposed toward the laryngoscope blade's trailing end, and a light pipe (46). The electrical light source (44) selectively contacts the electrical contact (34) in the operative intubation position for assisting intubation.

SUMMARY OF THE INVENTION

The present invention is for an ISO 7376/1 type metal laryngoscope blade including a resiliently elastically deformable metal blade hook-on fitting for removable double snap engagement into an operative intubation position on a metal laryngoscope handle including an electrical power source with first and second terminals with a correspondingly sized handle hook-on fitting, a metal spatula attached to the blade hook-on fitting and including a leading tip for transversely extending from the laryngoscope handle in the operative intubation position for insertion into a subject's mouth, and an illumination assembly including an electrical light source disposed toward the leading tip for providing illumination thereat for assisting intubation.

The illumination assembly includes a trailing connector for mounting in the blade hook-on fitting and rigid L-shaped plastic tubing extending between the trailing connector and the electrical light source having a pair of a first contact and a second contact. The plastic tubing guides a first electrically conducting wire for selective electrically connecting the first contact with the handle's first terminal in the operative intubation position and a second electrically conducting wire for electrically connecting the second contact with the handle's second terminal. The present invention affords a low cost secure illumination arrangement.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DESCRIPTION OF THE PREFERRED EMBODIMENTS OF THE PRESENT INVENTION

Figure 1:
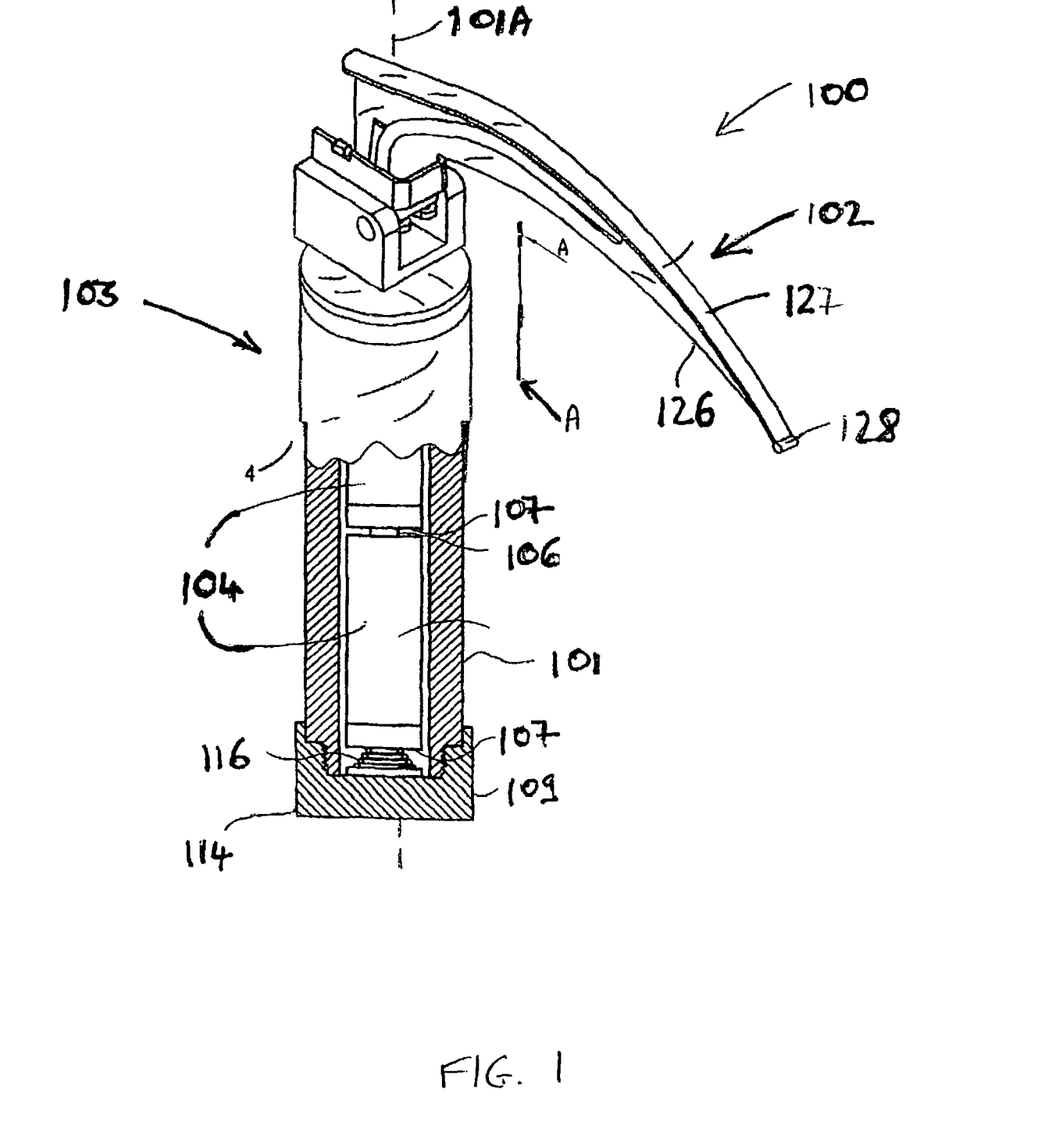
FIG. 1 is a pictorial view of an ISO 7376/1 type laryngoscope having a metal laryngoscope handle and a metal laryngoscope blade corresponding to aforesaid US 2007/0129606's FIG. 5.
Figure 2:
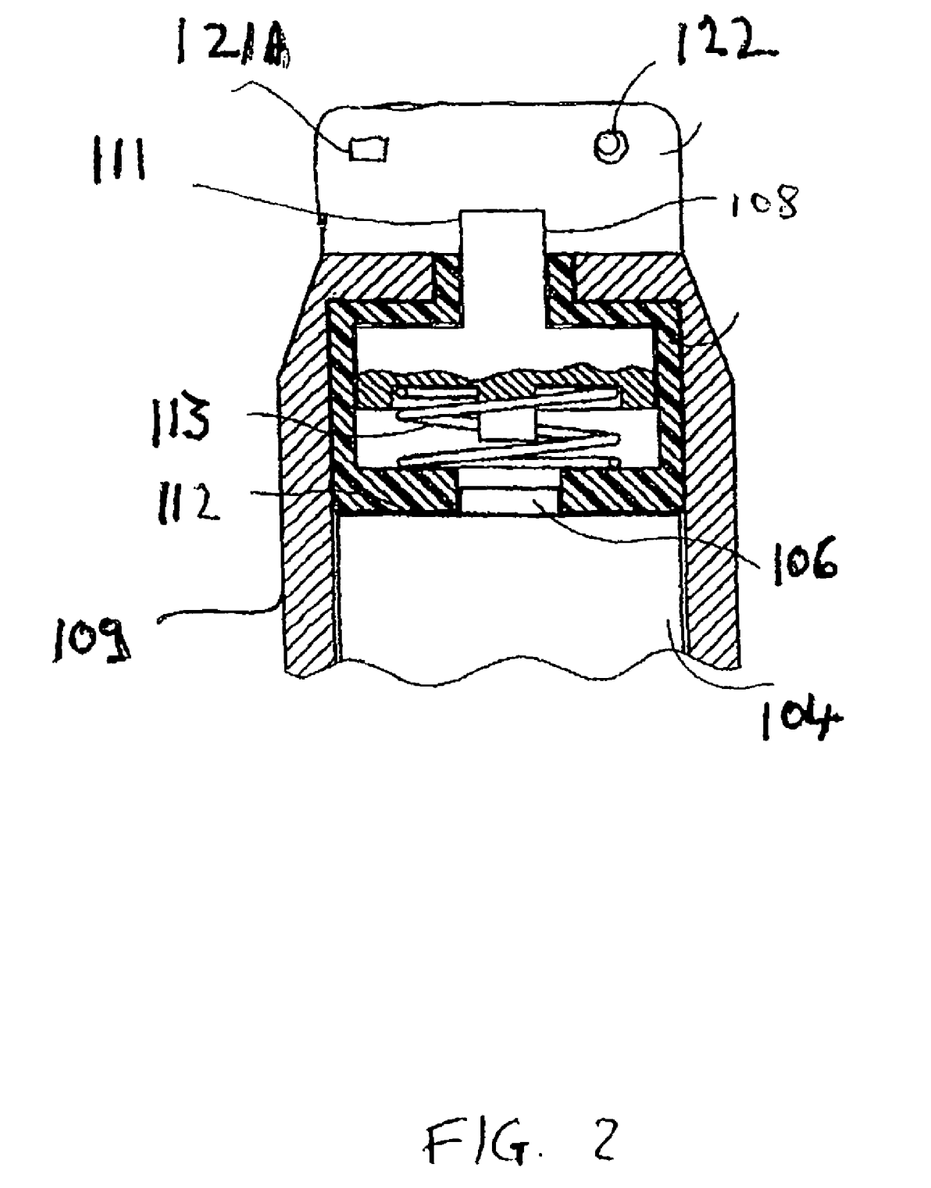
FIG. 2 is a longitudinal cross section of the top part of FIG. 1's handle along line A-A in FIG. 1.
Figure 3:
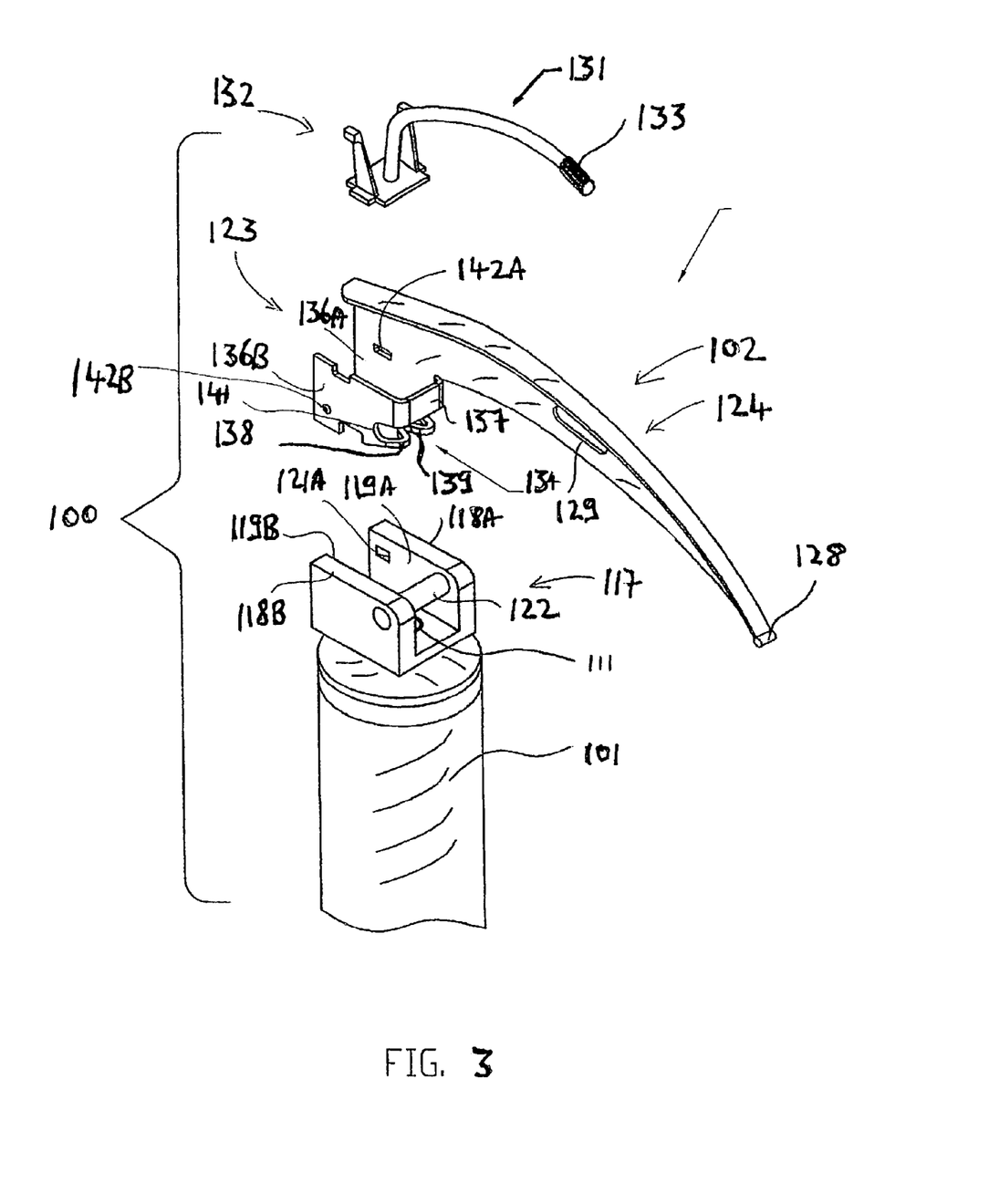
FIG. 3 is an exploded view of FIG. 1's laryngoscope.

FIGS. 1 to 3 show an ISO 7376/1 type laryngoscope 100 with a metal laryngoscope handle 101 with a longitudinal axis 101A and a metal laryngoscope blade 102 for removable double snap engagement onto the handle 101 for selective manipulation to an operative intubation position. The handle 101 houses an electrical power source 103 typically constituted by two standard size batteries 104 in series inserted with their positive terminals 106 directed toward the blade 102 and their negative terminals 107 directed away therefrom.

The power source 103 has a pair of opposite polarity terminals including a first electrical terminal 108 and a second electrical terminal 109. The first electrical terminal 108 is constituted by a metal contact pin 111 slidingly mounted in a tubular electrically insulating bushing 112 including a compression spring 113 for outwardly urging the metal contact pin 111 away from the leading battery's positive terminal 106. The second electrical terminal 109 is constituted by the metal laryngoscope handle 101 which is in electrical contact with the trailing battery's negative terminal 107 by means of a metal cap 114 having a metal compression spring 116 for urging the batteries 104 towards the blade 102.

The handle 101 has an upright U-shaped handle hook-on fitting 117 with a pair of spaced apart substantially parallel upright supports 118A and 118B with interior surfaces 119A and 119B having a pair of opposite recesses 121A and 121B, and a pivot rod 122 extending thereacross. The electrical terminal 108 is disposed midway between the pair of upright supports 118A and 118B co-axial with the longitudinal axis 101A.

The blade 102 includes a trailing blade end 123 in the form of a resiliently elastically deformable metal blade hook-on fitting for removable double snap engagement onto the handle hook-on fitting 117 and a stainless steel upright spatula 124 for transversely extending from the handle 101 in its operative intubation position for insertion into a subject's mouth. The spatula 124 includes a wide flange-like tongue engaging surface 126 and an opposite narrow flange-like teeth engaging surface 127 and tapers towards a leading tip 128. The spatula 124 includes an elongated opening 129 co-directional with the spatula 124 and disposed midway toward the leading tip 128. The blade 102 includes an L-shaped light guide mount 131 with a trailing connector 132 for snap fit insertion into the blade hook-on fitting 123 and a leading electrical light source 133 for insertion through the opening 129 such that the connector 132 and the light source 133 are on opposite sides of the spatula 124.

The blade hook-on fitting 123 has a thin walled U-shaped retaining member 134 facing toward the leading tip 128. The retaining member 134 has a pair of spaced apart substantially parallel side walls 136A and 136B, a major front crosspiece 137 extending widthwise between their upper leading portions, and a minor front bridge 138 bridging widthwise between their lowermost leading portions with a centrally disposed indentation 139 directed away from the leading tip 128 whereby the bridge 138 assumes a bifurcated appearance. The retaining member 134 is formed with a leading cutout 141 for snap insertion of the pivot rod 122 therein effected by the pivot rod 122 resiliently downwardly elastically deforming the bridge 138 relative to the crosspiece 137 as it passes over the indentation 139. The side walls 136A and 136B have exterior facing protrusions 142A and 142B disposed towards the trailing end of the blade 102 for snap insertion into their corresponding recesses 121A and 121B on positive snap manipulation of the blade hook-on fitting 123 fully into the handle hook-on fitting 117 whereupon the blade 102 assumes its operative intubation position.

Double snap fit engagement of the blade 102 on the handle 101 closes the electrical circuit connecting the power source 103 to the light guide mount 131 for powering the light source 133 for providing illumination at the leading tip 128 for assisting intubation.

Figure 4:
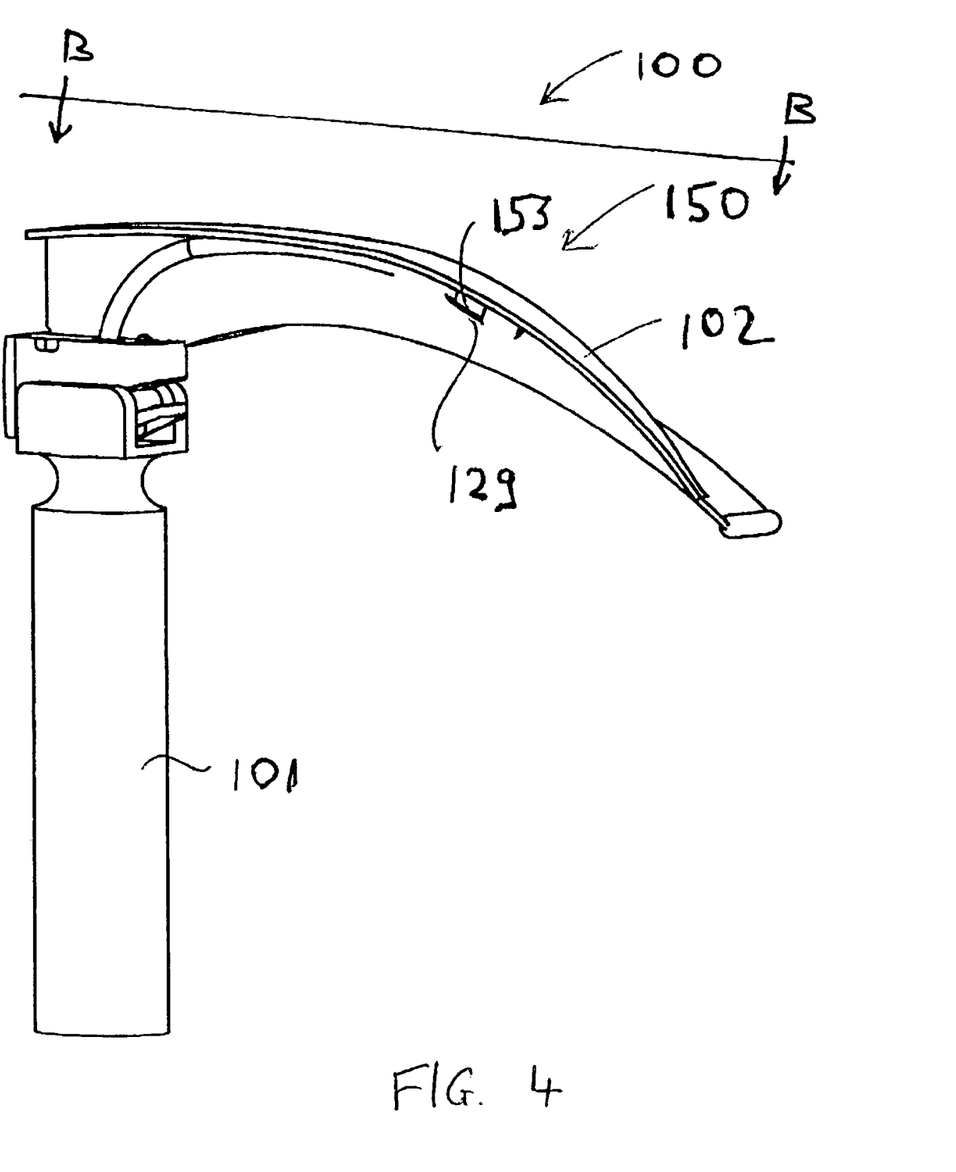
FIG. 4 is a pictorial view of an ISO 7376/1 type laryngoscope having a metal laryngoscope handle and a metal laryngoscope blade including an illumination assembly in accordance with the present invention
Figure 5:
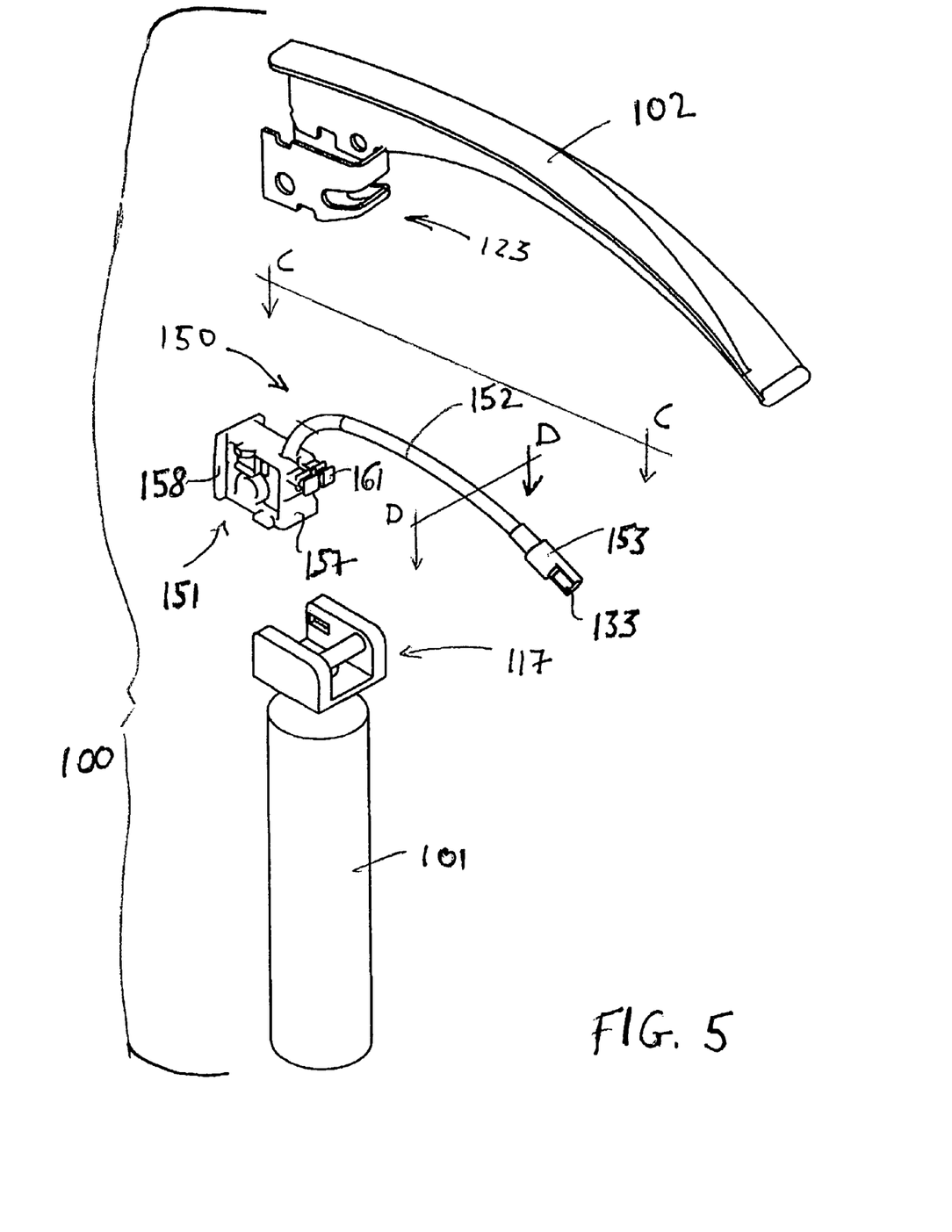
FIG. 5 is an exploded view of FIG. 4's laryngoscope.
Figure 6:
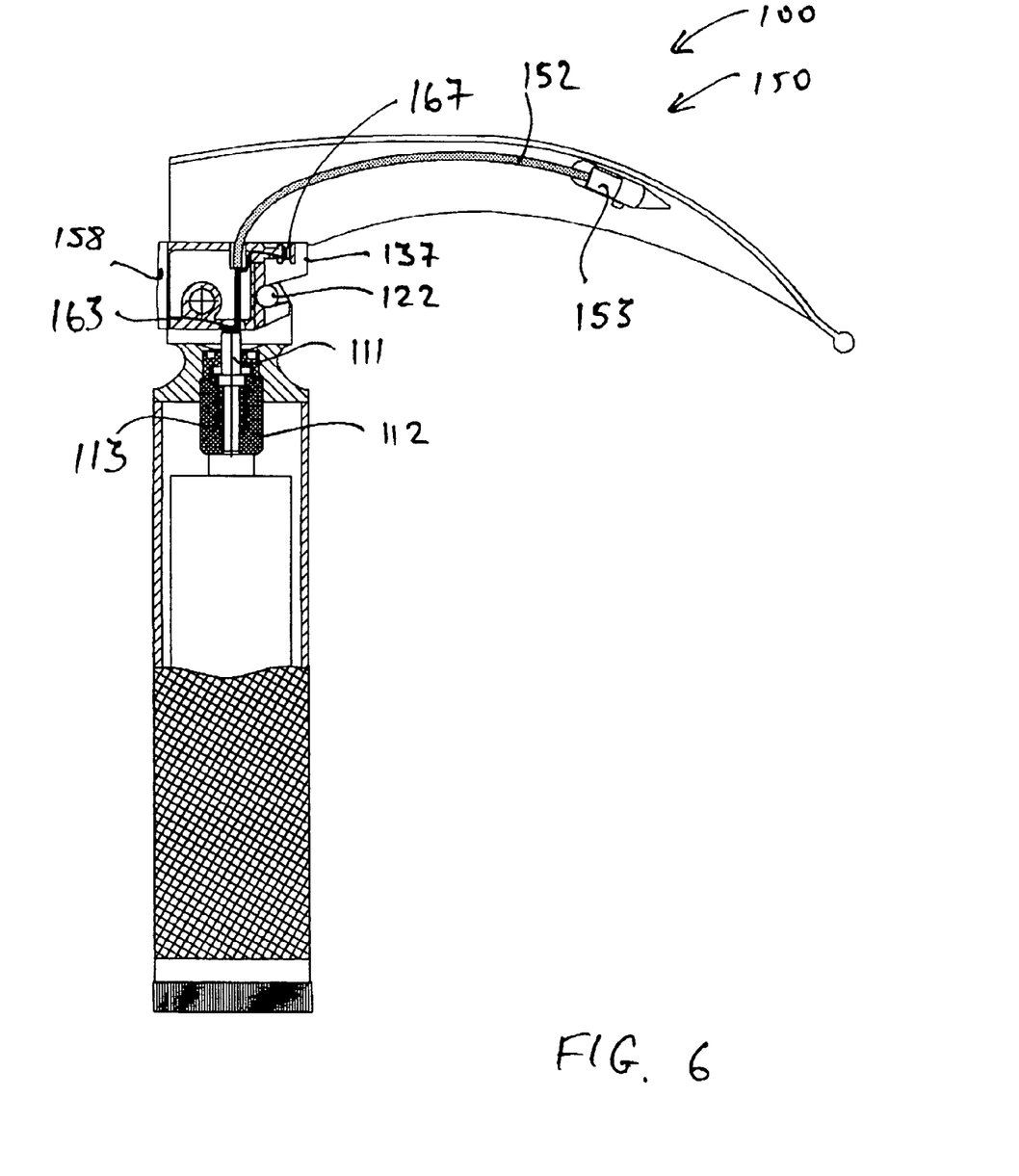
FIG. 6 is a longitudinal cross section of FIG. 4's laryngoscope along line B-B in FIG. 4.
Figure 7:
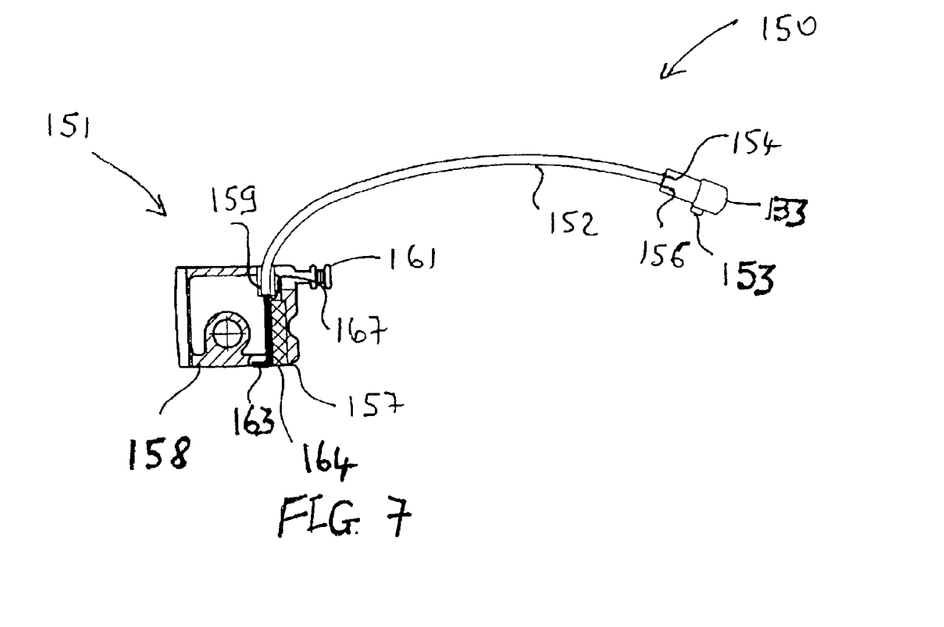
FIG. 7 is a transverse cross section of FIG. 4's illumination assembly along line C-C in FIG. 5.
Figure 8:
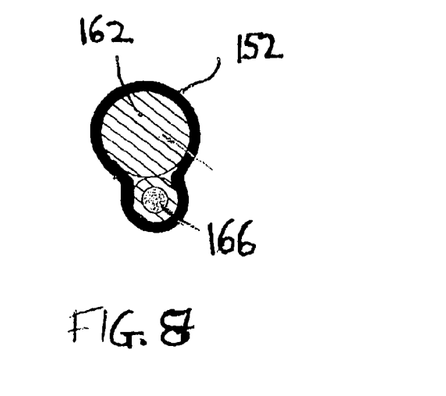
FIG. 8 is a transverse cross section of a first embodiment of FIG. 4's illumination assembly along line D-D in FIG. 5.

FIGS. 4 to 6 show the laryngoscope 100 with an illumination assembly 150 instead of the light guide mount 131. The illumination assembly 150 includes a trailing connector 151 for snap fit insertion into the blade hook-on fitting 123, a rigid L-shaped plastic tubing 152, and a light source housing 153 for housing the light source 133 having a first contact 154 and a second contact 156. The illumination assembly 150 can employ different approaches for ensuring sufficient structural strength for maintaining the rigidity of the plastic tubing 152. The light source housing 153 is interference fit urged through the elongated opening 129 on mounting the illumination assembly 150 onto the blade 102. The connector 151 snap fit inserted into the blade hook-on fitting 123 and the light source housing 153 interference fit urged through the elongated opening 129 securely fastens the illumination assembly 150 to the blade 102.

FIGS. 5 to 8 show the connector 151 includes a leading section 157 disposed toward the major front crosspiece 137 and a trailing section 158 disposed away therefrom. The leading section 157 includes a throughgoing bore 159 co-directional with the handle's longitudinal axis 101A on assembling the blade 102 on the handle 101 and a front protrusion 161 for abutting against the inside surface of the major front crosspiece 137. The trailing section 158 abuts against the trailing surfaces of the 136A and 136B on snap fit insertion of the trailing connector 151 into the blade hook-on fitting 123.

The plastic tubing 152 includes a first uncoated thick wire 162 extending from the first contact 154 via the throughgoing bore 159 and terminating at an exposed contact 163 for electrically contacting the metal contact pin 111 on assembling the blade 102 on the handle 101. The illumination assembly 150 includes a pin 164 inserted into the leading section 157 adjacent the contact 163 for securing the wire 162 in the connector 151. The plastic tubing 152 includes a second coated thin wire 166 extending from the second contact 156 and terminating in windings 167 wound around the protrusion 161 for continuous contact with the U-shaped retaining member 134. The plastic tubing 152 is preferably heat shrunk onto the wires 162 and 166. The wire 162 preferably has an about 13 to 14 AWG wire gauge and the wire 166 has an about 24 AWG wire gauge.

Figure 9:
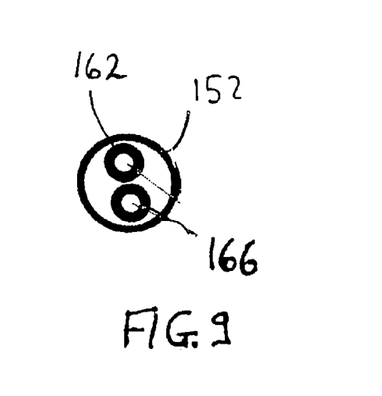
FIG. 9 is a transverse cross section of a second embodiment of FIG. 4's illumination assembly along line D-D in FIG. 5.

FIG. 9 shows an alternative arrangement for achieving rigidity of the plastic tubing 152. The plastic tubing 152 can be formed from suitably thick rigid plastic material guiding two wires 162 and 166 of the same about 24 AWG wire gauge. Suitable rigid plastic materials include rigid PVC, ABS, and the like.

Double snap fit engagement of the blade 102 on the handle 101 closes the electrical circuit connecting the power source 103 to the illumination assembly 150 for powering the light source 133 for providing illumination at the leading tip 128 for assisting intubation.

While the invention has been described with respect to a limited number of embodiments, it will be appreciated that many variations, modifications, and other application of the present invention can be made within the scope of the appended claims.

LIST OF PARTS

100 ISO 7376/1 type laryngoscope
101 metal laryngoscope handle
101A longitudinal axis
102 metal laryngoscope blade
103 power source
104 two standard size batteries
105 -
106 battery positive terminals
107 battery negative terminals
108 power source first electrical terminal
109 power source second electrical terminal
110 -
111 metal contact pin
112 electrically insulating bushing
113 compression spring
114 metal cap
115 -
116 metal compression spring
117 upright U-shaped handle hook-on fitting 118 spaced apart substantially parallel upright supports
119 interior surfaces
120 -
121 opposite recesses
122 pivot rod
123 trailing blade end in the form of a resiliently elastically deformable metal blade hook-on fitting
124 stainless steel upright spatula
125 -
126 wide flange-like tongue engaging surface
127 opposite narrow flange-like teeth engaging surface
128 leading tip
129 elongated opening
130 -
131 L-shaped light guide mount
132 trailing connector
133 electrical light source
134 thin walled U-shaped retaining member
135 -
136 spaced apart substantially parallel side walls
137 major front crosspiece
138 minor front bridge
139 centrally disposed indentation
140 -
141 leading cutout
142 exterior facing protrusions
143
150 illumination assembly
151 trailing connector
152 rigid L-shaped plastic tubing
153 light source housing
154 first contact
155 -
156 second contact
157 leading section
158 trailing section
159 throughgoing bore
160 -
161 front protrusion
162 first uncoated thick wire
163 exposed contact
164 pin
165 -
166 second coated thin wire
167 windings

The invention claimed is:

1. A metal laryngoscope blade for removable double snap engagement into an operative intubation position on a laryngoscope handle, and having a leading tip for insertion to a subject's larynx entrance area,
the laryngoscope handle having a longitudinal axis and including:
an upright U-shaped handle hook-on fitting including a pair of spaced apart substantially parallel upright supports with interior surfaces having a pair of substantially opposite recesses, a pivot rod extending thereacross, and
an electrical power source having a first electrical terminal disposed between the pair of spaced apart substantially parallel upright supports, the metal laryngoscope blade having a leading tip and comprising:
(a) a resiliently elastically deformable metal blade hook-on fitting including a thin walled U-shaped retaining member which includes facing toward the metal laryngoscope blade's leading tip, and including a pair of spaced apart substantially parallel side wall members providing a gap therebetween and a front crosspiece that extends across the gap and faces toward the metal laryngoscope blades leading tip, with a resiliently elastically deformable bridge extending widthwise across the gap between their leading lowermost regions for defining a cutout for snap receiving the pivot rod therein on positive snap manipulation of said blade hook-on fitting thereon, said side wall members having trailing regions with respect to said bridge having exterior surfaces at least one thereof being provided with a non-frangible metal protrusion integrally formed therewith for snap insertion into a handle hook-on fitting's recess on positive snap manipulation of the blade hook-on fitting fully into the handle hook-on fitting whereupon the laryngoscope blade assumes its operative intubation position;
(b) a metal spatula attached to said blade hook-on fitting and including said leading tip for transversely extending from the laryngoscope handle in the laryngoscope blade's operative intubation position for insertion into a subject's mouth; and
(c) an illumination assembly including an electrical light source disposed toward said leading tip and in selective electrical connection with the electrical power source in the operative intubation position for providing illumination thereat for assisting intubation.

2. The blade according to claim 1 wherein said illumination assembly further including a trailing connector for mounting in said blade hook-on fitting and rigid L-shaped plastic tubing extending between said trailing connector and said electrical light source having a pair of a first contact and a second contact, said plastic tubing guiding a first electrically conducting wire for selective electrically connecting said first contact with the handle's first electrical terminal in the operative intubation position and a second electrically conducting wire for electrically connecting said second contact with the handle's second electrical terminal.

3. The blade according to claim 2 wherein at least one wire of said first and second wires having a sufficient wire gauge for forming said rigid L-shape.

4. The blade according to claim 3 wherein said first wire has the sufficient wire gauge for forming said rigid L-shape.

5. The blade according to claim 2 wherein said plastic tubing is heat shrunk.

6. The blade according to claim 2 wherein said plastic tubing is formed from thick rigid plastic material with inherent rigidity to maintain said L-shape.

7. The blade according to claim 2 wherein said second wire terminates in windings in continuous contact with said resiliently elastically deformable metal blade hook-on fitting.

* * * * *